United States Patent
Pera

(10) Patent No.: US 6,845,777 B2
(45) Date of Patent: Jan. 25, 2005

(54) COMPOSITION TO REDUCE OR QUIT SMOKING ADDICTION

(76) Inventor: Ivo E. Pera, 1400 St. Charles Place, Pembroke Pines, FL (US) 33026

( * ) Notice: Subject to any disclaimer, the term of this patent is extended or adjusted under 35 U.S.C. 154(b) by 0 days.

(21) Appl. No.: 10/261,541

(22) Filed: Sep. 30, 2002

(65) Prior Publication Data

US 2003/0084912 A1 May 8, 2003

(30) Foreign Application Priority Data

Oct. 22, 2001 (EP) ............................................ 01125054

(51) Int. Cl.$^7$ ........................... A24F 47/00; A24B 15/00
(52) U.S. Cl. ......................... 131/270; 131/352; 131/347
(58) Field of Search ................................ 131/270, 359, 131/352, 347, 353, 356; 514/343; 424/400, 439, 451, 489

(56) References Cited

U.S. PATENT DOCUMENTS

| | | | |
|---|---|---|---|
| 5,055,478 A | | 10/1991 | Cooper et al. |
| 5,158,771 A | | 10/1992 | Spindler et al. |
| 5,656,255 A | * | 8/1997 | Jones ........................... 424/43 |
| 5,845,647 A | * | 12/1998 | O'Donnell, Jr. et al. .... 131/276 |
| 6,082,368 A | | 7/2000 | Brown |
| 6,138,683 A | * | 10/2000 | Hersh et al. ................. 131/347 |
| 6,470,894 B2 | * | 10/2002 | Hersh et al. ................. 131/334 |

* cited by examiner

Primary Examiner—Dionne A. Walls
(74) Attorney, Agent, or Firm—Daniel S. Polley, P.A.

(57) ABSTRACT

A method and composition to help persons reduce or quit smoking is disclosed, employing raw tobacco leaves, or tobacco fluid extract, or food grade tobacco like flavor and aroma, and Antioxidants, with or without and SAMe and caffeine. All ingredients can be in a micro-powdered or liquid form, for buccal administration. The composition can be in a tablet or capsule that is intended to be slowly sucked and dissolved in the mouth, and that delivers the nicotine, caffeine or SAMe, proved to be effective in alleviating smoking withdrawal symptoms. The composition can also be embedded inside a soft squeezable plastic cigarette for simulated smoking, providing additional periodic doses of nicotine, caffeine and SAMe to satisfy cravings for cigarettes.

27 Claims, No Drawings

COMPOSITION TO REDUCE OR QUIT SMOKING ADDICTION

This application claims the benefit of and priority to European Patent Application No. EP 01125054.5, filed in the European Patent Office on Oct. 22, 2001.

DESCRIPTION

1. Technical Field

The present invention relates to the technical sector of the production of substances useful to help persons to reduce or quit smoking. In particular, it concerns a novel composition containing tobacco or tobacco fluid extract or food grade, tobacco like flavor and aroma with antioxidants with/or without caffeine and/or SAMe.

2. Background Art

Tobacco is an annual plant with a long fibrous root, stem erect, round, hairy and viscid. It branches near the top and is from 3 to 6 feet high. Leaves are large, numerous, alternate, sessile, somewhat decurrent, ovate, lanceolate, pointed, entire, slightly viscid and hairy, pale-green color, brittle, narcotic odor, with a bitter acrid taste. By distillation with water it yields a concrete volatile oil termed nicotianin or tobacco camphor, which is tasteless, crystal-line and smells of tobacco; other constituent is the alkaloid nicotine, nicotianin, nicotinine, nicotine, nicoteline. After leaves are smoked the nicotine decomposes into pyridine, furfurol, collidine, hydrocyanic acid, carbon monoxide, etc. The poisonous effects of tobacco smoke are due to these substances of decomposed nicotine. Tobacco, if used as snuff, causes violent sneezing and also a copious secretion of mucous. Chewed, it increases the flow of saliva by irritating the mucous membranes of the mouth. In large doses it produces nausea, vomiting, sweats and great muscular weakness.

The alkaloid nicotine in high doses is a virulent poison, producing great disturbance in the digestive and circulatory organs. It innervates the heart, causing palpitation and cardiac irregularities and vascular contraction, and is considered one of the causes of arterial degeneration. Nicotine is very like coniine and lobeline in its pharmacological action, and the pyridines in the smoke modify very slightly its action. Tobacco was once used as a relaxant, but is no longer employed except occasionally in chronic asthma.

In "A modem herbal book" it is mentioned that tobacco is used as a sedative, diuretic, expectorant, discutient, and sialagogue, and internally only as an emetic, when all other emetics fail. The leaves in combination with the leaves of belladonna or *stramonium* make an excellent application for obstinate ulcers, painful tremors and spasmodic affections.

Tobacco smoking has become recognized over the last few decades as a major medical and social problem. This includes not only cigarette smoking, but also cigar and pipe smoking and smokeless tobacco use including chewing tobacco and snuff. Because of the medical problems associated with its use, the majority of tobacco users would like to stop or at least reduce the amount of tobacco consumed each day. In addition to the medical problems, there are also restrictions now relating to smoking in the work place and in public areas, such as restaurants and shopping centers, which also require smokers to exercise considerably greater control over their smoking habits.

However, many people find it virtually impossible, especially in the case of cigarettes, to control their tobacco habit. Where a person, for example, has stopped smoking cigarettes completely, there is often a continuous craving, and if that person tries to alleviate the craving by smoking even just one cigarette, he or she very quickly returns to his or her original level of consumption. Similarly, if one tries to cut down on the amount of tobacco used, such as the number of cigarettes smoked each day, the craving increases in intensity, and the smoker soon returns to the former level of use. Prior to this invention, tobacco users, especially smokers, had to rely on will power and complete abstention to manage their tobacco habit. There was no known drug that permitted the users to control effectively their craving or use of tobacco. By and large it is the impurities in tobacco and its smoke, which kill, while nicotine provides most of the pleasure, stimulation and relief from stress.

Tobacco smoking lowers the amount of oxygen that gets to the brain. While dilation of the blood vessels in the brain occurs immediately after cigarette smoking, chronic smoking slows the overall reduction in cerebral blood flow. It also causes vasoconstriction of the blood vessels in other areas of the body, and infuses the red blood cells with carbon monoxide, greatly reducing their oxygen-carrying capacity. In a sense, this constitutes a slow suffocation of the cells in the body and is far more pernicious than any possible benefit that might accrue from nicotine, which, as some research has shown, in small quantities may temporarily "wake up" certain aspects of memory.

Smoking also greatly increases the number of free radicals in the blood. Eventually it affects the lungs and hinders breathing, which depletes energy and strength. Although the effects of cigarette smoking on a variety of diseases, including cancer and cardiovascular illness and emphysema, have been well publicized, the effect of smoking on nutrients in the body are less widely known. Consider the destructive effects of cadmium, a toxic trace element as deadly as mercury and lead, and one of the components of tobacco. One pack of cigarettes yields 10 times the amount of cadmium the body is capable of assimilating, thus weakening the immune system. Cadmium get into tobacco in several ways, most commonly from growing tobacco in cadmium polluted soil, and is sprayed on tobacco as a fungicide. Even if you don't smoke, environmental exposure to tobacco smoke raises your blood concentration of cadmium. Israeli investigators found that the blood levels of cadmium in non-smokers exposed to cigarette, smoke was very close to the average found in smokers. Cadmium decreases the availability of selenium and inhibits the metabolism of zinc. Not only does smoking lower the level of Vitamin C and beta-carotene in the blood and reduces levels of Vitamin E and several B-complex vitamins in body tissues, but for unknown reasons smokers also are less likely to consume fruits and vegetables, particularly those high in Vitamin C and carotene.

Smokers all over the world are aware of the dangers they stand by continuing to smoke the regular types of cigarettes, cigars or the like. It has been proven that, the major damage to smokers is caused by residues of tar transferred by the inhaled smoke to the lungs, causing tar deposits on the lungs. These deposits are major causes for lung cancer and other incurable damages.

The partial oxidation that occurs during smoking to the paper or other cellulose parts in the cigarettes results in a large proportion of carbon monoxide in the released cigarette smoke. When the smoke is being inhaled these quantities of carbon monoxide enter the bloodstream, thus causing a reduction of available oxygen in the blood, and hence great disturbances to the heart function. It is well known that cigarette smoking is a major reason for several heart diseases.

It has therefore been the aim of many products to attract smokers away from smoking cigarettes, thus reducing the medical risks, yet retaining some of the pleasures caused by the supposed addiction to cigarettes. It has been proved that most smokers who wish to stop smoking are addicted to several features of the smoking procedures, namely:

The sensation of holding a mouthpiece and sucking it;

The taste of nicotine, the major aroma of tobacco;

The ritual of taking in and blowing out the smoke.

This invention is directed to help smokers reduce or quit smoking, more specifically it concerns itself with a novel composition which is designed to satisfy the psychogenic drives and pharmacological needs of the smoker, without subjecting the smoke, or other unwanted intrusions upon his person.

The potential ill-effect inherent in smoking cigarettes and other tobacco products are well documented and need not to be repeated here. Due to the recognized risks associated with smoking, the tobacco industry has introduced products having low tar and nicotine content, enhancing the efficiency of the filters on their filtered cigarettes, and labeling the cigarette pack, as directed by the Surgeon General of the United States Public Health service. All of this is to provide an information message warning the purchase of the health risks associated with smoking. All of the measures taken by the tobacco industry, the warning of the Surgeon General, the educational programs and messages from national associations concerned with heart disease and lung cancer, the incentives for medical/health insurance have done little to dissuade the habitual smoker from continuing to smoke. The reasons underlying his resistance to break this habit are threefold:

a) The psychological and social drives associated with smoking, namely, an apparent need or ritual involved in the lighting and holding of a cigarette and gratification derived by placing it in one's mouth.
b) To stimulate the act of puffing on a cigarette, and
c) The pharmacological effects of nicotine upon the body.

The mechanical steps involved in smoking include carrying cigarettes, lighting them, placing them between the lips, sucking on them, inhaling the smoke, exhaling, holding the lighted cigarette, and repeating the maneuver. A physical need that is satisfied by these steps is the achievement of a blood level of nicotine and other substances. This is somewhat that habituated smoker's body comes to sense a worthwhile goal. Psychological needs that are satisfied by the steps involved in smoking are very basic and infantile, including ingesting, sucking, grasping, and repetitive hand to mouth activity.

That the psychological needs of smoking are of as great importance as the chemical ones is amply illustrated by consistent observations on persons who have recently tried to quit. They eat more and gain weight, "do not know what to do" with their hands, and experience extreme psychological discomfort manifested as irritably. While the loss of chemical satisfaction contributed to this by unknown and indirect mechanisms, the substitution of food for smoking substitutes the importance of the sucking and ingestion behavior.

Many preparations have been devised to combat tobacco habits. These prior efforts have generally been directed to the concurrent use of tobacco and silver salts, sulfides, sulfur, thioglycols, lobeline, sedatives, anticonvulsant drugs, or other substances causing nausea or ill feeling to the end of building up to a psychological response to tobacco that make the same undesirable. Not only have such preparations proved unpopular because of the lack of desire on the part of the individual deliberately to make himself ill to cure the habit, they have also proved ineffective to many instances even when faithfully employed. It is well known that the habit-formula and health-deterring factor in tobacco (*Nicotiana Tabacum*) is the Nicotine ($C_{10}H_{14}N_2$) which is a very toxic substance, the lethal unit dose for an average adult is about 60 mg; one cigarette delivers about 1 mg. of nicotine. Nicotine is a volatile oil, inflammable, powerfully alkaline, with an acrid smell and a burning taste. Once nicotine enters the blood stream, it has been shown to cross the blood brain barrier and bind to receptors in the brain, resulting in the release of the neurotransmitter serotonin in the central nervous system's neurohumoral pathways.

One constituent of tobacco smoke: nicotine, is a stimulant to the central nervous system. Nicotine is one of the most powerful psychoactive drugs known, with addiction occurring when doses reach high levels. Smokers inhale approximately one milligram per cigarette, which quickly enters the bloodstream through the lungs, going straight to the brain. Here, it stimulates the brain, speeding up communication between cells. But by the time a cigarette is finished, the nicotine level in the blood begins to plunge, causing the body to urgently signal its need for more. Smoking a cigarette every half an hour or so keeps nicotine levels elevated, but the smoker pays a devastating price.

Nicotine probably is the reason why many people find smoking pleasurable and the reason many people become dependent on tobacco. Withdrawal from nicotine brings about unpleasant sensation likened to withdrawal from any drug. Nicotine produces widespread effects on both the central nervous system and the cardiovascular and peripheral systems. Nicotine addiction is established more rapidly than addiction of heroin. Almost any smoker claims that smoking helps him or her to calm down, to work better and to meet the daily stress with its apparent tranquilizing effect, but that is proved to be an illusion. Smoking doses not make a smoker less irritable or vulnerable to annoyance. Smoking a cigarette introduces nicotine into the system via the soft tissues of the mouth as well as through the lungs. The body reacts violently, since nicotine is a psychoactive drug. The reaction causes a flow of adrenaline and other hormones, which bring us to a high alert and gives us (briefly) increased energy in a crisis by elevating our blood-sugar level. This causes a momentary "lift", it is followed, however, by a too rapid movement of glucose out of the blood after the "danger" is past, and the result is a feeling of fatigue. Fatigue causes anxiety, self-pity, low grade dissatisfaction and general discomfort, which, for a smoker is a signal to reach for the pickup in a cigarette.

Consider the fact that this process is repeated twenty, thirty or forty times a day and for however many years a person smoke; if we could see inside our body, we will see a lot of action. In addition to glands squirting adrenaline, the pancreas is busily dealing with the glycogen and the blood pressure, which increase the heartbeat rate by at least 9 beats per minute (around 1000 extra beats per day), and all that activity apparently influences the levels of fats circulating in the bloodstream. At the same time, the red blood cells are obstructed for their mission of carrying oxygen to the heart and brain because of the carbon monoxide and other gases in the cigarette smoke. In fact, "as much as 20% of the blood pushed around by the heart of the smokers is not working so far as carrying oxygen is concerned. Since the heart has the highest oxygen requirement per unit weight of any tissue, any change in the supply of oxygen could affect the heart first, and thereby increase the risk of an attack for the smoker". Since nicotine is addictive, since the body requires that a certain level must be maintained in the blood-stream, the smoker becomes uncomfortable when he or she has gone beyond the normal time for another dose. Usually he or she reacts by reaching automatically for another cigarette. Switching to low-nicotine cigarette supply causes problem smokers to smoke more; zero-nicotine cigarettes are usually rejected.

Let's consider why people continue to smoke. They don't quit because smoking gives them certain benefits. Many campaigners for the elimination of cigarette smoking have not realized that people would lose these benefits, as well as the health risks. Tobacco has significant effects on behavior and psychological state. Recent research has shown that cigarette smokers (and others who use tobacco) find that tobacco use makes it easier to cope with over-stimulation like city noise and overcrowding. That's because the nicotine in cigarette smoke is a stimulus barrier, a substance that makes it easier for a person to function in an over-stimulating environment. Human brain-wave activity can be measured by putting electroencephalograph electrodes on a person's head. When a subject is subjected to a sudden unexpected stimulus (like a loud noise), you find out how much the brain responds to these stimuli. The brain of a person who has used nicotine responds less to these distracting stimuli than the brain of someone who doesn't smoke. In this way, the nicotine makes it possible for some people to cope with the over-stimulation found in most cites by reducing their brain's reactions to the extraneous stimulation.

While nicotine's effect on the neurotransmission of serotonin, and the receptors of the presynaptic membrane are poorly understood; it is believed that the abstinence from tobacco and nicotine results in the re-up-take and accumulation of serotonin in these neurohumoral pathways, that when the release of which is not stimulated by nicotine, results in the symptoms of nicotine withdrawal. The symptoms included restlessness, irritability, anxiety, drowsiness, increasingly frequent waking from sleep, impatience, confusion, impaired concentration, carbohydrate craving and weight gain, impaired reaction time and a craving for tobacco; this craving for tobacco is the overwhelming reason why so many individuals who try to quit smoking fail to succeed. Pharmacological therapies are known to help, those addicted to nicotine, but most of the therapies are unsatisfactory because they have short term effect as well as numerous undesirable side-effects.

Nicotine is readily absorbed by all of the body's tissues, including the skin, the respiratory epithelium, and the mucous membranes of the mouth, nose and intestines. The present invention Tobacco-Antioxidants composition's absorption through the mouth, depends too on the pH level or in effect, the acidity of the saliva present, with a more acidic saliva changing nicotine molecules into a ionic form that is not well absorbed. Similarly nicotine entering the acidic medium of the stomach cannot easily move across cellular membranes, again reducing absorption, while in the alkaline medium of the small intestine, the molecules reverts to soluble, nonionic state, easily passing through the intestinal wall. From there nicotine undergoes extensive metabolism in the liver, the resulting products, or metabolites, of this process being primarily cotinine and nicotine n-oxide. Consequently, only about 30% of nicotine from the intestine reaches the bloodstream in a not metabolized form.

In contrast, inhalation of tobacco smoke allows a greater amount of active nicotine to pass into the circulatory system. (As much as 90% of the nicotine inhaled from a cigarette is absorbed into the bloodstream). From the bloodstream the compound passes to the heart, which pumps a significant portion of the nicotine directly to the brain, the transfer is so rapid, in fact, that nicotine in tobacco smoke reaches the brain more quickly than does nicotine injected directly into the bloodstream through as vein.

After a brief rise, the brain's nicotine concentration quickly falls as the compound is speedily redistributed to the other parts of the body. Some researchers believe that the bolus of nicotine in each puff of tobacco inhaled from a cigarette reinforces the nicotine habit in the brain, probably by releasing a small amount of dopamine, so that hundreds of puffs per day reinforces the addiction hundreds of times per day. Nicotine readily crosses the placental barrier as well, resulting in fetal exposure to the compound when women smoke during pregnancy. Additionally, nicotine can pass into breast milk, albeit in very low levels. Possessing a relatively short duration of action within the body, nicotine has a plasma half-life of between 30 minutes and 2 hours (meaning that half of the blood's nicotine levels disappear within this span of time). In nicotine-dependent cigarette smokers, who typically smoke every 30 to 45 minutes, blood nicotine levels rise cumulatively during the day before leveling off. Peak levels in the arteries, which deliver the drug to the brain, often reach approximately 40 micro-grams per milliliter of blood. Although most nicotine in the body is metabolized in the liver, the compound is also eliminated through excretion in urine, passing into it from the bloodstream according to changes in urinary acidity. Lowering of the pH, that is, making the urine more acids, as happens in stressful situations or through an increased intake of vitamin C, increases nicotine excretion, decreasing the compound's levels more rapidly.

Since cotinine, nicotine's major metabolite, has a much longer half-life than its parent compound, lasting from 10 to 40 hours, its presence in the body is commonly used to determine whether an individual's smoking cessation efforts have been successful.

As blood nicotine levels decline, the nicotine-dependent smoker begins to experience sense of craving, this typically being a cue to reach for another cigarette. Since inhaled nicotine is absorbed so rapidly, smokers can adjust (titrate) their blood nicotine levels within a satisfying range not only by controlling the timing and number of cigarettes consumed but also by altering the way in which each cigarette is smoked, that is, the duration of each puffs, the depth of smoke inhalation, and the length of time that smoke is held in the lungs.

Nicotine may be tied to the onset of cardiovascular disease, based on the ability of sharp increases in blood nicotine levels to encourage blood clotting, inflation of blood lipid levels, and stimulation of a portion of the accomplishes this last action by raising blood levels of catecholamines, comprising adrenaline and similar compounds. Yet direct evidence association low levels of nicotine with cardiovascular disease is weak, and when nicotine is absorbed slowly, it does not appear to increase cardiovascular risk or cause adverse cardiac effects, even in patients with coronary artery disease.

During surveys conducted in industrialized nations, most participating smokers expressed a desire to give up tobacco and in many cases, revealed that they had tried to do so, with the first few attempts commonly ending in relapse. This relapse can be traced at least in part to the nicotine withdrawal syndrome, which exists when at least four of the following signs occur within 24 hours of an abrupt cessation of a reduction in nicotine use: (a) a dysphoric or depressed mood; (b) insomnia; (c) irritability, frustration, or anger; (d) anxiety; (e) difficulty in concentrating; (f) restlessness; (g) a decreased heart rate; and (h) an increased appetite or weight gain.

Despite this litany of adverse effects, epidemiological studies also indicate that smoking may afford some protection against the development of both Parkinson's disease, caused by the death of certain dopamine containing brain cells, and Alzheimer's disease. There is also some evidence that smoking decreases the change of developing ulcerative colitis, an inflammatory bowel disease.

On a more positive note, not necessarily speaking against tobacco and according to my research for alternate use of tobacco in agriculture, I have evaluated the potential of tobacco as a source of leaf protein and use its protein for food plus as a safer alternative choice to smoking, considering the yield by the hectare of leaf proteins can be at least four times higher than that of seed proteins and that the proteins contained in the amino acids are circa 9% Aspartic Acid, 5.2% threonine, 3.1% serine, 11.5% glutamic acid, 5.1% proline, 10.3% glycine, 9.4% alanine, 8% valine, 1.2% valine, 1.2% methionine, 4.5% isoleucine, 8.9% leucine, 4.4% tyrosine, 4.1% phenylalanine, 6% lysine, 2.8% histidine, and 6.5arginine. Leaves contain 0.6 to 0.9% alkaloids, including nicotine, nornicotine, anabasine and anataline; roots also contain most of these alkaloids. Leaves also contain the aromatic nicotianin (tobacco camphor).

By weight proteins are the major component of the dry material of a living organism and they are among the most important functional components of the living cells. Proteins are the building blocks of the body and are required for the growth, repair and maintenance of cells, which are constructed from proteins. Proteins are needed for the manufacture of hormones, antibodies, enzymes and tissue. The major cause of poor nutritional value is due to a low content or unavailability of one or more of the indispensable amino acids.

More recent study of the smoking problem has led to the development of Nicotine gums or patches, as anti-smoking aids. As a general practice that alternative nicotine sources are only effective as anti-smoking aid when an individual immediately stops smoking and substitutes the nicotine source for the cigarette. The problem with nicotine substitution therapy involves the administration of the psychoactive constituent of tobacco indicates as a contributor to the diseases for which smoking is a risk factor.

Administering just nicotine as a substitute of smoking have not been successful because these methods do not recognize and address the two-prong "addiction" of smoking. First, there are social and psychological reasons for smoking that must be initially overcome. Secondly, there is the more powerful psychological than pharmacological reason (nicotine addiction) that must then be conquered. Both the social and psychological causes of smoking, as well as the pharmacological nicotine dependence must be addressed in sequence, if a truly successful method of eliminating an individual's tobacco smoking habit and associated nicotine dependence is to be provided.

Caffeine—The stimulant effects that are attributed to nicotine, including those characterizing its addictive nature, are also attributed to caffeine, hooked. One-half of the world's population, consumes caffeine in tea, and another one third get their fix from coffee. Millions more find daily doses in soft drinks. Caffeine's origin in soft drinks has a botanical basis: caffeine is a component of the kola nut from which Coca Cola was originally derived. However, modem beverages of many brands are purposely spiked with the drug. Like nicotine, caffeine is found naturally in plants, like tea, coffee, kola, nuts, and cacao beans (from which cocoa and chocolate are made). In fact, it is even placed in the same general chemical class as nicotine. But the similarities do not end there. The table below compares the effects of nicotine with those of caffeine, the similarity is self explanatory.

| Nicotine | Caffeine |
|---|---|
| Brain: | |
| Stimulant | Stimulant |
| Enhances concentration | Enhances concentration |
| Enhances performance | Enhances performance |
| Sense of well being | Sense of well being |
| Mood elevation | Mood elevation |
| Addictive: | Addictive: |
| Psychic dependence | Psychic dependence |
| Withdrawal | Withdrawal |
| Tolerance | Tolerance |
| Stimulates breathing Center | Stimulates breathing Center |
| Circulatory: | |
| Increases heart rate | Increases heart rate |
| Increases blood pressure | Increases blood pressure |
| Constricts blood vessels | Constricts blood vessels |
| Other: | |
| Increases: | Increases: |
| Free fatty acids | Free fatty acids |
| Catecholamine release | Catecholamine release |
| Saliva and lung secretion | Stomach acids |
| | Urine flow |

Consumers of caffeine do not suffer heath effects that can be easily associated with their addiction. Although caffeine affects almost every organ system in the body, producing (relatively minor and positive) mental and physical effects, it is consumed in a relatively safe manner.

S-Adenosyl-Methionine (SAMe)—Many scientists have known for years that most of us do not get all the vitamins we need from our food and that the RDA levels of many vitamins are absurdly low. We also know that the levels of folate and SAMe in the blood of many people are too low for their optimum health, mental and physical. Likewise, we know that homocysteine levels in the upper half of the normal range are a risk factor for many diseases, including hearth attack.

Unfortunately today it is considered normal to have a heart attack even at a young age. However, today thank to SAMe many, if not most heart attacks and strokes are almost entirely preventable! In fact, the basic process of vascular disease, artherosclerosis and athrosclerosis is largely preventable.

SAMe is a naturally occurring molecule that is part of all living cells, and affect so many different aspects of human biology and pathology being a metabolic helper that is produced during methylation and facilitates nearly all methylation reactions in your body. As one of the primary methyl group donors, SAMe is extremely important and historically unappreciated. One of its many roles is methylating DNA. When DNA is properly laced with methyl groups, your cells are protected form the abnormal expression of DNA, a behavior associated with disease and aging. Aside from this sole in DNA methylation, SAMe also acts as a natural antidepressant, possibly through its role in creating the neurotransmitter melatonin. Clinical studies have long shown oral intake of SAMe to have antidepressant effects.

SUMMARY OF THE INVENTION

The main object of the present invention aims to help smokers to reduce slowly tobacco smoking addiction and thereby abate smoking related harm. Moreover the object is based upon the idea that since nicotine is the chemical reinforcement of the smoking habit, it might be possible to produce a chewable tablet containing Tobacco-Antioxidants in a micro-powdered form, which would satisfy the smoker's craving for nicotine without exposure to harmful ingredients developed by the tobacco combustion.

An object of the present invention is to slowly substitute tobacco smoking with a Tobacco-Antioxidants formulation to be ingested. The underlying reasoning is simple and correct; it is the smoke from a cigarette, not the nicotine, that causes disease. Yet, Tobacco-Antioxidants tablets easily provide enough nicotine to satisfy smokers craving and pose a minimal health risk to anyone. This risk is estimated to be less than two percent as large as the risk associated with smoking. And as fringe benefits, the Tobacco-Antioxidants formulation pose no risk to anyone else and its use is sufficiently discreet that the user will not be ostracized in any way.

Accordingly, the objective which underlines this invention is to provide a Tobacco-Antioxidants composition which in a relatively short time will induce the smoker to smoke less due to the strong aversion to smoking provoked by the good feeling and satisfaction in chewing the present composition. The non-toxic components of this invention produce a strong satisfactory nicotine effect, while helping to reduce the harm caused by tobacco smoke. The Tobacco-Antioxidants composition of the present invention is a major advance in treatment for smokers. It reduces withdrawal effects, enhances success in short-term cessation, reduces relapse if use is not curtailed too soon, and roughly doubles long-term success rates compared with placebo and various psychological methods. The aroma and tobacco flavors included in the formulation produce a pleasant and desired fragrance and have a sweeter spicy, wood-oriental, Virginia hay tobacco notes and taste, with much more body and much more natural tobacco-like aroma prior and during chewing or ingesting the formulation of the present invention.

Recent discoveries about Antioxidants substances have caused great optimism in the search for allies in the fight against cancer, the most important, and particularly effective for the prevention and/or treatment of tobacco related diseases are the Antioxidants. Antioxidants offer us some protection against lung cancer and cancer of the esophagus. They may also help ward off colon, rectal, bladder, prostate, breast, cervical, larynx, gastrointestinal and skin cancers, among others. The evidence to support these claims comes from worldwide studies of populations with diets full of food rich in Vitamin C, Vitamin E and Beta-carotene, as well as from laboratory studies of the vitamin's ability to prevent cancers in experimental animals. Antioxidants appear to have such powerful anticancer effects that the cancer establishment has started clinical trials for its use in the treatment of cancer as well as for its prevention. Such prevention seems to be particularly effective in the case of bronchogenic squamous carcinoma, since the latter has a long latency period during which metaplasia slowly develops.

Surveys conducted in the U.S.A. and several European Universities revealed that smokers with diets deficient in Antioxidants had twice as much lung cancer as smokers whose Antioxidants & Vitamins intake was not deficient. At first, these patients were treated with high doses of conventional anti-cancer drugs, but they suffered from side effects of this therapy before any effect on their cancer could be documented. When researchers started experimenting with beta-carotene and retinoic acid derivatives a sensible improvement was immediately noted. Recommended Daily Allowance (RDA) of Antioxidants provides to build a strong protection against free radicals.

While the present invention has been described with reference to use orally a Tobacco and Antioxidants Composition it will be understood by those skilled in this art that various other antioxidants not included in the following list can be used without departing from the spirit of the invention. Thus, the composition of the invention can include one or more of the following and/or one or more other antioxidants: Acetyl-L-Carnitine, Adenosine, Allicin, Aloe, Alpha Lipoic Acid, BHA, BHT, Bilirubin, Capsaicin, Catalases, Catechin, Cysteine, Coenzyme Q10, Copper Sebacate, Coumarin, Curcumin, Dimethylglycine, Glycine, Ferrous Fumarate, Folic Acid, Genistein, Ginger, Ginko Biloba, Gallates, Gluconate, Glutathione or Glutathione Peroxidase, Green Tea, Inositol, Isoascorbic Acid, L-Glutamine, Linoleic Acid, L-Methyl Methionine, L-Seleno Cysteine, L-Seleno Methionine or Methionate, Lycopene, Lutein, Manganese, Melatonin, Methionine Reductase w/(Cu—Zn or Mn), N-Acetylcysteine or L-Cysteine, N-Acyl 1-Cysteine Esters, N-Acyl 1-Methionine Esters, Poplar Bud, Procyanidin, Pycnogenol, Resveratrol, Rosemary, Rutin, Rutinose, Selenium-Yeast, Seleno Cysteine, Seleno Methionine or Methionate, Silybum Marianum, Sodium Bisulfite, Sodium Metasulfite, Sodium Sulfite, Sodium Thiosulfite, Spirulina, Sulfuraphane, Superoxide Dismutase (SOD), Taurine, Thioglycerol, Thiol, Thiosorbitol, Thiourea, Vitamin A compounds, Vitamin B2 compounds, Vitamin B6 compounds, Vitamin B12 compounds, Vitamin C compounds, Vitamin E compounds, Wheat Grass and/or Zinc Gluconate.

It is reasonable to expect that we can stay healthier and live longer, increasing life expectancy 20 or more years, while possible increasing the maximum life span slightly beyond 100 years, if we curtail free radical activity using in our diet various radical scavengers as above listed.

There is a group of amino acids, vitamins, minerals and enzymes called antioxidants that have been shown in laboratory tests to help in protecting the body from the formation of free radicals, inhibiting the development of cancer. At the National Cancer Institute there has been established a test to identify the most powerful antioxidants useful to prevent cancer, and up-to-date several hundreds of them have been found, that might do something to influence cancer risk, and over fifty of the most promising ones are further being tested in animal models. Many important studies that further solidify the connection between smoking cancer, free radicals, and antioxidants continue to proliferate.

The response to this blizzard of scientific support seems clear: a sound comprehensive Antioxidant program is necessary to achieve the best chance for continuing good health. Another important ingredient of the compostion is S-Adenosyl-L-methionine (SAMe) which intimately is involved with trans-sulfuration, a process that produces a supremely important substance in our bodies called glutathione. Sometimes called the "Master Antioxidant", glutathione is at the center of the body defense system that controls those ubiquitous scoundrels in our bodies known as free radicals (Free radicals are not a rebellious political action group that takes over our bodies, but for all thee damage they do, they might as well be.). Free radicals are the unstable molecules in our bodies and unstable oxygen molecules that are generated by the basic chemical transaction of living: oxidizing calories into energy. When these free radicals accumulate in our systems, the results can be deadly: they can attack our DNA with the possible result of cancer, they can attack the lipids in our blood causing them to turn into the plaque that blocks our arteries and causes heart attacks and strokes; and they can attack brain cells, causing senility.

Thankfully, antioxidants are the natural enemies of free radicals and that is why a diet rich in antioxidants like vitamins C, E, and beta carotene, and L-glutathione is recommended to promote health by protecting against the diseases borne of an overpopulation of free radicals. But better yet is SAMe: It is essential for the trans-sulfuration process that is the source of the internal production of glutathione. Beside functioning as an antioxidant, glutathione also plays an important anti-inflammatory role in our systems.

Further and perhaps mot importantly, without SAMe the liver is unable to produce the antioxidant glutathione causing the free radicals to multiply and abet the proliferation of toxins in the body, including the liver itself, being proved its natural anti-inflammatory effect in our body. SAMe is one of the most vital links to health known today in maintaining not only health but in preventing diseases. Therefore, the composition object of the present invention may be presented in a new form suitable for oral administration. The administration of the composition may be solid or liquid and may take the form of micro-powder granules, sparkling powder, tablets, coated tablets sparkling tablets, capsules, gel, lozenges, syrups, emulsions, suspensions, elixirs or drops.

In a preferred embodiment the present invention proposes to use uncured tobacco leaves as a raw material preferably as soon as harvesting to generate a composition that retains the natural attributes of the plant, nicotine, proteins, chlorophylls, and several enzymes. The tobacco leaves can be used as picked, or they may be dried at preferably no more than about 150° C. (though other temperatures above and below are considered within the scope of the invention) before processing. The Tobacco-Antioxidants Composition of this invention can be prepared by the methods commonly employed using conventional organic or inorganic additives such as an excipient (e.g. sucrose, starch, mannitol, sorbitol, lactose, glucose, cellulose, talc, calcium, phosphate, calcium carbonate, etc. and the like), a binder (e.g. methilcellulose, hydroxymethilcellulose, polypropylpyrollidone, polyvinylpyrollidone, gelatin, gum arabic, polyethyleneglycol, etc. and the like), a disintegrator (e.g. carboxymethylcellulose, hydroxypropylstarch, sodium bicarbonate, calcium phosphate, calcium citrate, etc. and the like), a lubricant (e.g. magnesium stearate, light anydrous silicic acid, talc, sodium lauryl sulphate, etc. and the like), a flavoring agent (e.g. citric acid, menthol, glycine, orange powder, etc. and the like), a preservative (e.g. sodium benzoate, sodium bisulfite, methylparaben, propylparaben, etc. and the like), a stabilizer (e.g. citric acid, sodium citrate, acetic acid, etc. and the like), a suspending agent (e.g. methylcellulose, polyvinylpyrrolidone, aluminum stearate, etc. and the like), a dispensing agent (e.g. hydroxypropylmethyl cellulose, etc. and the like), a diluent (e.g. water, etc. and the like) and base wax (e.g. cocoa butter, white petrolatum, polyethylene glycol, etc. and the like).

The composition of the present invention can be prepared as micro-powder form to provide an effective dose of Tobacco and Antioxidants in capsules, tablets, sparkling powder or any other form suitable for oral administration, having at least two or more active ingredients, with each one preferably individually being a powerful free radical scavenger with an amount at least sufficient for total dosage requirement during a treatment period. Of course this can greatly vary depending upon the relative amount of the ingredients. In more details the composition can comprise at least two therapeutically active substances, being homogeneously incorporated into any such substance in a solid or nonsolid state. Furthermore, if required, the therapeutic usefulness of the present composition for oral administration can be improved by using one of any suitable controlled sustained release formulation, which can be used in preparation of the compositions in order to obtain the required controlled rate in the digestive system.

The Tobacco-Antioxidants composition can include a plurality of ingredients mixed in proportions obtaining a micro-powdered mixture, that is pleasant to the taste, which diminishes or obviates slowly the desire to use tobacco. The Tobacco-Antioxidants composition provides a scientifically proven treatment to help smokers to slowdown the habit of the physical dependence on nicotine, avoiding nicotine withdrawal symptoms, simply reducing the nicotine in the blood. The Tobacco-Antioxidants Composition will help gradually reduce the body need of nicotine responding at the same time to overcome the psychological factor of non-smoking because the chewing provides a pleasing taste and smell to the user.

During the slow sucking and swallowing, of the tablet or capsule of the present Tobacco-Antioxidants composition, the smokers substitute the need of a cigarette with its tobacco taste flavor and with a small amount of nicotine, but in sufficient quantity to avoid the unpleasant sensation like irritability, drowsiness, anxiety, restlessness, headaches, stomach upset, difficulty to concentrate, normally resulting from the total nicotine withdrawal.

In the Tobacco-Antioxidants composition, the quantity of nicotine is far less than the quantity found in a cigarette but while it satisfies the smokers' psychological need, will also be of great beneficial health help to avoid the inhalation of other toxic, irritating chemicals found in cigarette during smoking such as tar and carbon monoxide, reducing the risk of cancer. Who finds impossible to quit smoking at all, will still benefit from reducing the number of cigarette smoked per day with the assistance of the Tobacco-Antioxidants composition. In this way, the person who is trying to drop the smoking habit has an occupation for the mouth, and the ingestion and inhalation of the antioxidants aromatic flavors, nicotine and other ingredients included in the gum or tablet will satisfy its need of nicotine, knowing that is actually chewing mild tobacco leaves and antioxidants useful in the prevention of smoke related diseases.

The continued use of the Tobacco-Antioxidants composition enables smokers over an extended period of time to gradually kick the smoking habit, and is constantly available to help to prevent reaction when smokers face new stress situations. Because they are getting most of their nicotine from the Tobacco-Antioxidants composition, some subjects have showed a sharp drop in the use of nicotine compared with their customary cigarette consumption, indicating this approach to smoking reduction and with time cessation is likely to be feasible. The Tobacco-Antioxidants composition contains substantial amount of active ingredients and flavor, which significantly preserves the useful functions of the active ingredients and flavor, reducing its diffusion rate and volatility, having a soft gel consistency from which the ingredients may escape for performing its functions.

Another type of controlled release formulation, which may be used, is that which is produced by a process involving micro-encapsulation techniques. Another particular feature of the Tobacco-Antioxidants composition is to be not only several time more, effective of tobacco chewing gum in slowing the release of flavor, but it delivers a continuous rich, full and true flavor for a long period of time, exceeding skilled several fold any gum composition heretofore known to those skilled in the art. The Tobacco-Antioxidants composition can be used over a prolonged period of time without noticeable toxic or harmful effects. With the Tobacco-Antioxidants composition smokers at last have available a safe partial substitute for conventional cigarettes.

Another object of the present invention is to provide a novel method to reduce or eliminate tobacco smoking habit, as well as the Nicotine dependency associated with that habit. The method includes the step of gradually decreasing tobacco consumption over several weeks until no further tobacco is desired. In brief, the smoker should record the time, during which each cigarette is consumed during the day, thereby reflecting his or her tobacco consumption pattern. Then after, the smoker gradually should decrease steadily the number of cigarettes to be smoked during the day. The best results are obtained if the reduction is at least one (1) cigarette per each succeeding weeks. For a smoker who consumes approximately thirty (30) cigarettes per day, the present method to reduce smoking at least 50% or more after thirty (30) to sixty (60) weeks. Starting from the first day the Tobacco-Antioxidants compound under subject is gradually ingested by the smoker and slowly chewed during the day with an increasing dose as a substitute for all cigarettes not smoked.

This serves to greatly reduce the intense craving, restlessness and irritability of the individual. As a result, the individual's confidence in breaking the stopping habit and the associated nicotine dependence grows. Since the tobacco consumption is decreased gradually there is less a trauma for the individual, such as anxiety, irritability or other adverse symptoms are reduced to a minimum.

Like nicotine, caffeine is found naturally in plants like tea, coffee, kola nuts, and cacao beans (from which cocoa and chocolate are made). In fact, it is even placed in the same general chemical class as nicotine. Dried ripe seeds of coffee are the source of caffeine (approximately or about 0.7 to approximately or about 2%). In humans, caffeine, 1,3,7-trmethylxanthine, is demethylated into three primary metabolites: theophyllne, theobromine and paraxanthine. Since the early part of the $20^{th}$ century theophyllne has been used in therapeutics for bronchodilatation, for acute ventricular failure and for long-term control of bronchial asthma.

Caffeine ($C_8H_{10}N_4O_2$) is used orally as a mild CNS stimulant to aid in staying awake and to restore mental alertness in fatigued patients. It stimulates all levels of the central nervous system. In oral doses of about 100 to about 200 mg., it stimulates the cerebral cortex producing a more rapid and clear flow of thought, wakefulness or arousal in fatigued patients and improved by psycomotor coordination. Its cortical effects are milder and of shorter duration than those of amphetamines. In slightly larger doses, caffeine stimulates medullary vagal, vasomotor and respiratory centers, including bradycardia, vasoconstriction and an increased respiratory rate.

Caffeine exerts multiple effects on the heart. It has a positive inotropic effect on the myocardium and a positive chronotropic effect on the sinoatrial node, causing a transient increase in heart rate, force of contraction, cardiac output and work of the heart. In doses of excess of about 250 mg. the centrally mediated vagal effects of caffeine may be masked by increased sinus rates, tachycardia, extrasystoles or other ventricular arrhythmias may result. Caffeine constricts the cerebral blood vessels but directly dilates peripheral blood vessels; thus, it decreases peripheral vascular resistance. The effect of this decrease in vascular resistance on blood pressure is compensated for by increased cardiac output. Thus the overall effect of caffeine on heart rate and blood pressure is dependent on whether the central nervous system or peripheral effects predominate. In most instances, therapeutic doses of caffeine increase blood pressure only slightly.

Other pharmacological effects of caffeine include the following:
stimulate voluntary skeletal muscle, increasing the force of muscle contraction and decreasing muscular fatigue; they stimulate parietal cells, increasing gastric acid and secretion; they induce a mild diuresis by increasing renal blood flow and glomerular filtration rate and decreasing proximal tubular re-absorption of sodium and water; and stimulate glycogenolysis and lipolysis, but the increases in blood glucose and plasma lipids usually are not significant in normal patients.

DETAILED DESCRIPTION OF THE PREFERRED EMBODIMENT

The invention provides an effective antismoking Tobacco-Antioxidants composition which can consist of tobacco leaves or Tobacco flavor, and various antioxidants (listed earlier in this disclosure), with or without caffeine and SAMe, and other ingredients for administration in unit dosage form, such as chewing gums, tablets, capsules, pills, powders, granules, liquid solutions micro-encapsulated or in suspensions. For oral administration, either solid or fluid unit dosage forms can be prepared, but most preferable in capsule or chewable tablet. A provision of the invention is also the provision to use the present composition in a liquid form embedded inside a soft squeezable plastic cigarette for simulated smoking.

It is well known to entray in bulk polymers or microcapsules to attain controlled sustained release of a permeant. Examples may be found in my U.S. Pat. No. 4,906,488 which is incorporated herein by reference. Therefore, another innovative feature of the Tobacco-Antioxidants composition involves the utilization of my Micro-Imbibed Polymer-Flavor Sponge technology to overcome the disadvantage found in a chewable gum or tablet available on the market (i.e. that when chewed the initial perception of the flavor contained in, appear at a low after a minute or more, that increase and after four or five minutes of chewing the flavor intensity drop to an uninteresting level to slowly disappear). With my process the tobacco flavor and other ingredients added to the Tobacco-Antioxidants compound provide an almost instantaneous tobacco flavor release with an extended high intensity constant, continuous uninterrupted tobacco flavor perception time and with evenly and uniformly controlled release of all active ingredients over an extended period of time.

Such method, moreover substantially reduces, the diffusion rate, volatility or susceptibility to oxidation or other form of environmental attack upon the tobacco or other flavor, and is effective in lengthening the shelf life of the composition by preserving the entire composition for a longer period of time.

For preparing solid compositions such as tablets, the principal active ingredient is mixed with conventional ingredients such as, but not limited to, talc, magnesium stearate, dicalcium phosphate, magnesium aluminum silicate, calcium sulfate, starch, lactose, acacia, methylcellulose, and functionally similar materials as pharmaceutical diluents or carriers. The tablets can be coated or otherwise compounded to provide a dosage form affording the advantage of prolonged or delayed action or predetermined successive action of the enclosed medication. For example, the tablet can comprise an inner dosage and an outer dosage component, the latter can be in the form of an envelope over the former. The two components can be separated by an enteric layer, which serves to resist disintegration in the stomach and permits the inner component to pass intact into the duodenum or to be delayed in release. A variety of materials can be used for such enteric layers or coatings such materials including a number of polymeric acids or mixture of polymeric acids with such materials as shellac, cetyl alcohol, cellulose acetate phthalate, styrene maleic acid copolymer and the like. Wafers can be prepared in the same manner as tablets, differing only in shape and in the inclusion of sucrose or other sweetener and flavor. In their simplest embodiment, capsules, like tablets, can be prepared by mixing the compound of the formulation with an inert pharmaceutical diluent and filling the mixture into a hard gelatin capsule of appropriate size. In another embodiment, capsules are prepared by filling hard gelatin capsules with polymeric acid coated beads containing the compound of the formula. Soft gelatin capsules can be prepared by machine encapsulation of a slurry of a herbal compound preferably having an acceptable vegetable oil, light, liquid petrolatum or other inert oil.

Fluid unit dosage forms for oral administration such as syrups, elixirs, and suspensions can be prepared. The water-soluble forms of the herbal composition can be dissolved in an aqueous vehicle together with sugar, aromatic flavoring agents and preservatives to form a syrup. An elixir can be prepared by using a hydro-alcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose and the like.

The term "unit dosage form" as used in the specification and claims, refers to physically discrete units suitable as unitary dosages for human subjects, each unit containing a quantity (which can be predetermined) of active ingredients (tobacco for its nicotine content and one or more antioxidants) as free radical scavenger calculated to produce the desired relief effect, and can be in association with the required flavors, diluent colorants, buffers or other conventional additives, carrier or vehicle. The specifications for the novel unit dosage forms of this invention can be dictated by and directly dependent on (a) the unique characteristics of the active ingredients and the particular relief effect to be achieved and (b) the limitation inherent in the art of compounding such active ingredients for therapeutic use in humans.

However, due to differences in smoking patterns, a heavy smoker may require more dosage for the first few weeks. This is generally sufficient to reduce a smoker's desire or need of tobacco. The objective to help people reduce or lose their craving for tobacco, which can be successfully reached using the Tobacco-Antioxidants composition of the present invention, and which can contain the following components in the amount indicated by weight percentage.

The following are examples of compositions prepared in accordance with this invention, but it is to be understood that they are presented by way of illustration only, and the dosage form and frequency of dosage of these forms can and may vary according to the type of tobacco used and nature and severity of the condition to be treated. The following examples should not be in anyway construed to limit the scope of the present invention. The two or three active ingredients of the nutraceutical formulation prepared according to the present invention, can consist of Tobacco leaves, tobacco fluid extract or food grade tobacco like aroma and flavour, Antioxidants, with or without SAMe and Caffeine, in a Micro Dry Powder form or liquid to be used by ingestion, administration which can comprise the percentages hereinafter described or fraction thereof:

From about or approximately 1% to about or approximately 85% by weight (and all numerical ranges therebetween) of one or more Antioxidants substance, From about or approximately 1% to about or approximately 65% by weight (and all numerical ranges therebetween) of tobacco leaves From about or approximately 0.01% to about or approximately 5% (and all numerical ranges therebetween) caffeine, and From about or approximately 0.01% to about or approximately 5% (and all numerical ranges therebetween) SAMe.

The preferred formulations comprise:

About or approximately 20% by weight of one or more Antioxidants substance, about or approximately 20% by weight of tobacco leaves, about or approximately 5% SAMe and about or approximately 5% caffeine all in a dry powdered form or liquid, plus the required necessary additives and flavours.

As a dietary supplement each Tobacco Antioxidants dose, as a main active ingredient object of the present invention, can contain a low dose of nicotine less than about or approximately 5 mg. and most preferably from about or approximately 0.5 to about or approximately 2 mg (and all numerical ranges therebetween). to avoid accidental overdosage and Antioxidants from about or approximately 30 mg. to about or approximately 100 mg (and all numerical ranges therebetween). The addition of caffeine as stimulant and mood lifter in the formulation of the present invention, will increase considerably nicotine levels and effects. Such synergetic result consequently will reduce a great deal the quantity of tobacco leaves required without caffeine.

In summary, numerous benefits have been described which result from employing the concepts of the invention. The method reduces the stress to which an individual is subjected during the process of stopping smoking. Specifically, the method allows the individual to first overcome the social and psychological causes for smoking and then, and only then, is there a need to address and overcome the nicotine dependency associated with smoking. By approaching these causes one at a time, individuals can successfully stop smoking. The tobacco-antioxidants composition can be part of an overall stop-smoking program that also may include behavior modification, counseling and support. The use of the cigarette substitute of the present invention also causes salivation, gastric acid secretion, and stimulation of the cranial nerve endings in the tongue, in like fashion to the stimulation caused by smoking cigarette and the like. Other physical effects also occur in the body as a result of the use of the present invention, including perhaps the production of endorphins in the bloodstream.

The foregoing description of a preferred Tobacco-Antioxidants Compound of the invention has been presented for purposes of illustration and description. It is not intended to be exhaustive or to limit the invention to the precise form disclosed. Obvious modifications or variations are possible in light of the above teaching. For example, various phases of the method may be adjusted in length in order to reflect differences in the smoking patterns of the individual.

The Tobacco-Antioxidants Compound was chosen and described to provide the best illustration of the principles of this invention and its practical application to thereby enable one of ordinary skill in the art to utilize the invention in various embodiments and with various modifications as are suited to the particular use contemplated. All such modification and variations are within the scope of the invention as determined by the appended claims when interpreted in accordance with the breadth to which they are fairly, legally and equitably entitled. As set forth the single ingredients of the Tobacco-Antioxidants Compound object of this invention are more effective when taken all together, nevertheless each of the ingredients can be used singularly concurrently with the use of tobacco.

Although the present invention has been described in a practical and possibly preferred form, it is to be understood that departures may be made therefrom within the scope of the present invention which is not to be limited to the details disclosed herein, but is to be accorded the full scope of the appended claims so as to embrace any and all equivalent compositions and methods. The suggested method of eliminating an individual's tobacco smoking habit and associated nicotine dependence in regulated matter, of course comprising the step of:

breaking a day down into smoking periods;
recording the number of cigarettes smoked;
reducing weekly the number of cigarettes smoked;
administering the dosage of the Tobacco-Antioxidants compound as alternative replacement of a cigarette, to gradually decreasing the amount of cigarettes to be gradually decreasing the amount of cigarettes to be gradually decreasing the amount of cigarettes to be smoked, while if necessary increasing the administration of the Tobacco-Antioxidants composition until the nicotine, the caffeine or SAMe administrations and smoking habit has been successful reduced or cured.

The invention can have the following characteristics:

1. A composition to help persons reduce or quit tobacco smoking, which comprises a Tobacco-Antioxidants formulation, with or without raw uncured tobacco in powdered form or tobacco fluid extract or a food grade tobacco like aroma and flavors, or SAMe and Caffeine, which can include as main ingredient Antioxidants derived from one or more amino acids, enzymes, chemicals, hormones, plants extracts, proteins, and when slowly dissolved in the mouth it gives a dose of nicotine almost equal to a cigarette, suitable for oral administration.

2. Composition of characteristic 1 that can be administered orally and is effective in preventing or curtailing very early stage diseases, in tobacco smokers.

3. Composition of characteristic 1 where the ingredients for administration are in unit dosage form, such as chewing gums, tablets, capsules, pills, powders, granules, liquid solutions or suspensions.

4. Composition of characteristic 1 where the composition can be used embedded inside a soft squeezable plastic cigarette for simulated smoking.

5. Composition of characteristic 1 where the composition can be prepared by employed conventional organic or inorganic additives and flavors.

6. Composition of characteristic 1 where the flavor can be preferably tobacco and the additives can be an excipient, a preservative, a stabilizer, a suspending agent, a dispensing agent, a diluent and/or a base wax.

7. Composition of characteristic 1 where the tobacco can be in liquid flavor or in liquid or powdered form and one or more antioxidants with or without other ingredients or additives and flavors.

8. Composition of characteristic 1, where the antioxidant(s) can be selected from one or more of the following Antioxidants: Acetyl-L-Carnitine, Adenosine, Allicin, Aloe, Alpha Lipoic Acid, BHA, BHT, Bilirubin, Capsaicin, Catalases, Catechin, Cysteine, Coenzyme Q10, Copper Sebacate, Coumarin, Curcumin, Dimethylglycine, Glycine, Ferrous Fumarate, Folic Acid, Genistein, Ginger, Ginko Biloba, Gallates, Gluconate, Glutathione or Glutathione Peroxidase, Green Tea, Inositol, Isoascorbic Acid, L-Glutamine, Linoleic Acid, L-Methyl Methionine, L-Seleno Cysteine, L-Seleno Methionine or Methionate, Lycopene, Lutein, Manganese, Melatonin, Methionine Reductase w/(Cu—Zn or Mn), N-Acetylcysteine or L-Cysteine, N-Acyl 1-Cysteine Esters, N-Acyl 1-Methionine Esters, Poplar Bud, Procyanidin, Pycnogenol, Resveratrol, Rosemary, Rutin, Rutinose, Selenium-Yeast, Seleno Cysteine, Seleno Methionine or Methionate, Silybum Marianum, Sodium Bisulfite, Sodium Metasulfite, Sodium Sulfite, Sodium Thiosulfite, Spirulina, Sulfuraphane, Superoxide Dismutase (SOD), Taurine, Thioglycerol, Thiol, Thiosorbitol, Thiourea, Vitamin A compounds, Vitamin B2 compounds, Vitamin B6 compounds, Vitamin B12 compounds, Vitamin C compounds, Vitamin E compounds, Wheat Grass and/or Zinc Gluconate.

9. Composition of characteristic 1 where the composition contains *Nicotiana tabacum* leaves reduced in a dry powdered form, which contain between about 2% to about 8% of Nicotine.

10. Composition of characteristic 1 where the composition contains tobacco fluid extract with or without nicotine.

11. Composition of characteristic 1 where the composition contains Food Grade Tobacco like Aroma and Flavor and sugar.

12. Composition of characteristic 1 where the S-Adenosyl-L-Methionine (SAMe) aids in the production of the master oxidant Glutathione, which is a bona-fide treatment for diseases at their source, of which each dose preferably does not exceed about 200 mg, though such value is not considered limiting.

13. Composition of characteristic 1 where the Caffeine acts as a central stimulant, of which each dose preferably does not exceed 100 mg, though such value is not considered limiting.

14. Composition of characteristic 1 wherein in liquid form it can contain water, soft drink and/or fruit juices.

15. Composition of characteristic 1 wherein in liquid form it can contain beer, coffee, chocolate and/or alcoholic drink.

16. Composition can comprise the following percentages: (1) from about or approximately 1% to about or approximately 85% by weight (and all numerical ranges therebetween) of one or more Antioxidants substance, (2) from about or approximately 1% to about or approximately 65% by weight (and all numerical ranges therebetween) of tobacco leaves; (3) from about or approximately 0.01% to about or approximately 5% by weight (and all numerical ranges therebetween) caffeine, and (4) from about or approximately 0.01% to about or approximately 5% by weight (and all numerical ranges therebetween) SAMe.

17. Composition can preferably comprise (1) about or approximately 20% by weight of one or more Antioxidants substance, about or approximately 20% by weight of tobacco leaves, about or approximately 5% by weight SAMe and about or approximately 5% by weight caffeine all in a dry powdered form or liquid, plus the required necessary additives and flavours.

The invention provides a method and composition to help persons reduce or quit smoking is disclosed, employing raw tobacco leaves, or tobacco fluid extract, or food grade tobacco like flavor and aroma, and antioxidants, with or without and SAMe and caffeine. All ingredients can be in a micro-powdered or liquid form, for buccal administration. The composition can be in a tablet or capsule that is intended to be slowly sucked and dissolved in the mouth, and that delivers the nicotine, caffeine or SAMe, proved to be effective in alleviating smoking withdrawal symptoms, characterized by anxiety, irritability, unpaired concentration and confusion. The smoker can also be helped to quit or limit the amount of cigarettes smoked, the composition can be embedded inside a soft squeezable plastic cigarette for simulated smoking, providing additional periodic doses of nicotine, caffeine and SAMe to satisfy cravings for cigarettes. Meanwhile the user is inhaling a strong pleasant tobacco sweet scent and swallowing a delicious aroma, meanwhile the antioxidants will provide a strong protection against free radicals.

The short-term, more physically satisfying solution that will save more lives sooner remains the antioxidants and tobacco composition object of the present invention, providing satisfaction of psychogenic drive to satisfy the craving for cigarette, to help people quit or reduce smoking cigarettes.

While the invention has been described and disclosed in certain terms and has been illustrated by disclosure of certain embodiments or modifications, persons skilled in the art who have acquainted themselves with the invention will appreciate that it is not necessarily limited by such terms nor to the specific embodiments and modifications disclosed herein. Thus, a wide variety of alternatives, suggested by the teachings herein, can be practiced without departing from the spirit of the invention, and rights to such alternatives are particularly reserved, especially those which fall within the scope of the appended claims.

What is claimed is:

1. A composition to help a person reduce or quit tobacco smoking, comprising the following ingredients:
   a tobacco element, said tobacco element being tobacco leaves or tobacco extract
   at least one Antioxident; and
   SAMe.

2. The composition of claim 1 further comprising caffeine.

3. The composition of claim 1 wherein said at least one Antioxidant is selected from one or more of the following: Acetyl-L-Carnitine, Adenosine, Allicin, Aloe, Alpha Lipoic Acid, BHA, BHT, Bilirubin, Capsaicin, Catalases, Catechin, Cysteine, Coenzyme Q10, Copper Sebacate, Coumarin, Curcumin, Dimethylglycine, Glycine, Ferrous Fumarate, Folic Acid, Genistein, Ginger, Ginko Biloba, Gallates, Gluconate, Glutathione or Glutathione Peroxidase, Green Tea, Inositol, Isoascorbic Acid, L-Glutamine, Linoleic Acid, L-Methyl Methionine, L-Seleno Cysteine, L-Seleno Methionine or Methionate, Lycopene, Lutein, Manganese, Melatonin, Methionine Reductase w/(Cu—Zn or Mn), N-Acetylcysteine or L-Cysteine, N-Acyl 1-Cysteine Esters, N-Acyl 1-Methionine Esters, Poplar Bud, Procyanidin, Pycnogenol, Resveratrol, Rosemary, Rutin, Rutinose, Selenium-Yeast, Seleno Cysteine, Seleno Methionine or Methionate, Silubum Marianum, Sodium Bisulfite, Sodium Metasulfite, Sodium Sulfite, Sodium Thiosulfite, Spirulina, Sulfuraphane, Superoxide Dismutase (SOD), Taurine, Thioglycerol, Thiol, Thiosorbitol, Thiourea, Vitamin A Compounds, Vitamin B2 Compounds, Vitamin B6 Compounds, Vitamin B12 Compounds, Vitamin C Compounds, Vitamin E Compounds, Wheat Grass or Zinc Gluconate.

4. The composition of claim 1 wherein the ingredients are provided in unit dosage form.

5. The composition of claim 4 wherein said unit dosage form is selected from one of the following: chewing gums, tables, capsules, pills, powders, granules, liquid solutions, suspensions, or embedded inside a soft squeezable plastic cigarette.

6. The composition of claim 1 wherein the ingredients are prepared by employing one or more organic or inorganic additives.

7. The composition of claim 6 wherein said one or more additives is chosen from the following: an excipient, a preservative, a stabilizer, a suspending agent, a dispensing agent, a diluent or a base wax.

8. The composition of claim 1 wherein the ingredients are prepared by employing one or more flavors.

9. The composition of claim 8 wherein said one or more flavor is tobacco.

10. The composition of claim 1 wherein said tobacco element is in a liquid form.

11. A composition to help a person reduce or quit tobacco smoking, comprising the following ingredients:
    a tobacco element, said tobacco element being tobacco leaves or tobacco extract;
    at least one Antioxidant;
    SAMe; and
    caffeine.

12. The composition of claim 11 wherein the ingredients are provided in unit dosage form selected from one of the following: chewing gums, tables, capsules, pills, powders, granules, liquid solutions, suspensions, or embedded inside a soft squeezable plastic cigarette.

13. The composition of claim 11 wherein the ingredients are prepared by employing one or more organic or inorganic additives and one or more flavors.

14. The composition of claim 13 wherein said one or more additives is chosen from the following: an excipient, a preservative, a stabilizer, a suspending agent, a dispensing agent, a diluent or a base wax.

15. The composition of claim 13 wherein said one or more flavor is tobacco.

16. The composition of claim 11 wherein said tobacco element is in a liquid form or powdered form.

17. The composition of claim 11 wherein said tobacco element contains *Nicotiana tabacum* leaves reduced in a dry powdered form, which contains between about 2% to about 8% of Nicotine.

18. The composition of claim 11 wherein an amount of said SAMe is about 200 mg or less.

19. The composition of claim 11 wherein an amount of said caffeine is about 100 mg or less.

20. The composition of claim 11 wherein said at least one Antioxidant is selected from one or more of the following: Acetyl-L-Carnitine, Adenosine, Allicin, Aloe, Alpha Lipoic Acid, BHA, BHT, Bilirubin, Capsaicin, Catalases, Catechin, Cysteine, Coenzyme Q10, Copper Sebacate, Coumarin, Curcumin, Dimethylglycine, Glycine, Ferrous Fumarate, Folic Acid, Genistein, Ginger, Ginko Biloba, Gallates, Gluconate, Glutathione or Glutathione Peroxidase, Green Tea, Inositol, Isoascorbic Acid, L-Glutamine, Linoleic Acid, L-Methyl Methionine, L-Seleno Cysteine, L-Seleno Methionine or Methionate, Lycopene, Lutein, Manganese, Melatonin, Methionine Reductase w/(Cu—Zn or Mn), N-Acetylcysteine or L-Cysteine, N-Acyl 1-Cysteine Esters, N-Acyl 1-Methionine Esters, Poplar Bud, Procyanidin, Pycnogenol, Resveratrol, Rosemary, Rutin, Rutinose, Selenium-Yeast, Seleno Cysteine, Seleno Methionine or Methionate, Silubum Marianum, Sodium Bisulfite, Sodium Metasulfite, Sodium Sulfite, Sodium Thiosulfite, Spirulina, Sulfuraphane, Superoxide Dismutase (SOD), Taurine, Thioglycerol, Thiol, Thiosorbitol, Thiourea, Vitamin A Compounds, Vitamin B2 Compounds, Vitamin B6 Compounds, Vitamin B12 Compounds, Vitamin C Compounds, Vitamin E Compounds, Wheat Grass or Zinc Gluconate.

21. A composition to help a person reduce or quit tobacco smoking, comprising the following ingredients:
 a tobacco element, said tobacco element being tobacco leaves or tobacco extract;
 at least one Antioxidant;
 SAMe in an amount of about 200 mg or less; and
 caffeine in an amount of about 100 mg or less.

22. The composition of claim 21 wherein the ingredients are provided in unit dosage form selected from one of the following: chewing gums, tables, capsules, pills, powders, granules, liquid solutions, suspensions, or embedded inside a soft squeezable plastic cigarette.

23. The composition of claim 21 wherein the ingredients are prepared by employing one or more organic or inorganic additives and one or more flavors; wherein said one or more additives is chosen from the following: an excipient, a preservative, a stabilizer, a suspending agent, a dispensing agent, a diluent or a base wax; wherein said one or more flavor is tobacco.

24. The composition of claim 21 wherein said tobacco element is in a liquid form or powdered form.

25. The composition of claim 21 wherein said tobacco element contains *Nicotiana tabacum* leaves reduced in a dry powdered form, which contains between about 2% to about 8% of Nicotine.

26. The composition of claim 21 wherein said at least one Antioxidant is selected from one or more of the following: Acetyl-L-Carnitine, Adenosine, Allicin, Aloe, Alpha Lipoic Acid, BHA, BHT, Bilirubin, Capsaicin, Catalases, Catechin, Cysteine, Coenzyme Q10, Copper Sebacate, Coumarin, Curcumin, Dimethylglycine, Glycine, Ferrous Fumarate, Folic Acid, Genistein, Ginger, Ginko Biloba, Gallates, Gluconate, Glutathione or Glutathione Peroxidase, Green Tea, Inositol, Isoascorbic Acid, L-Glutamine, Linoleic Acid, L-Methyl Methionine, L-Seleno Cysteine, L-Seleno Methionine or Methionate, Lycopene, Lutein, Manganese, Melatonin, Methionine Reductase w/(Cu—Zn or Mn), N-Acetylcysteine or L-Cysteine, N-Acyl 1-Cysteine Esters, N-Acyl 1-Methionine Esters, Poplar Bud, Procyanidin, Pycnogenol, Resveratrol, Rosemary, Rutin, Rutinose, Selenium-Yeast, Seleno Cysteine, Seleno Methionine or Methionate, Silubum Marianum, Sodium Bisulfite, Sodium Metasulfite, Sodium Sulfite, Sodium Thiosulfite, Spirulina, Sulfuraphane, Superoxide Dismutase (SOD), Taurine, Thioglycerol, Thiol, Thiosorbitol, Thiourea, Vitamin A Compounds, Vitamin B2 Compounds, Vitamin B6 Compounds, Vitamin B12 Compounds, Vitamin C Compounds, Vitamin E Compounds, Wheat Grass or Zinc Gluconate.

27. A composition to help a person reduce or quit tobacco smoking, comprising the following ingredients:
 a tobacco element, said tobacco element being tobacco leaves or tobacco extract and
 SAMe.

* * * * *